United States Patent [19]
Haddad et al.

[11] Patent Number: 5,570,709
[45] Date of Patent: Nov. 5, 1996

[54] DENTAL DEVICE

[75] Inventors: Gaby M. Haddad; Malika I. Haddad, both of Coquitlam, Canada

[73] Assignee: Jinah Gaby Haddad, Coquitlam, Canada

[21] Appl. No.: 282,646

[22] Filed: Jul. 29, 1994

[51] Int. Cl.⁶ .......................... A61C 15/04; A61C 17/00
[52] U.S. Cl. .............................................. 132/322; 433/88
[58] Field of Search ............................ 132/322; 433/80, 433/88

[56] References Cited

U.S. PATENT DOCUMENTS

| | | | |
|---|---|---|---|
| 3,144,867 | 8/1964 | Trupp et al. | 433/88 |
| 3,472,247 | 10/1969 | Borsum et al. . | |
| 4,031,908 | 6/1977 | Ting . | |
| 4,326,549 | 4/1982 | Hinding . | |
| 4,859,182 | 8/1989 | Nerli | 433/80 |
| 4,950,160 | 8/1990 | Karst | 433/88 |
| 4,957,436 | 9/1990 | Ryder | 433/88 |
| 4,984,984 | 1/1991 | Esrock | 433/88 |
| 5,033,961 | 7/1991 | Kandler et al. . | |
| 5,082,444 | 1/1992 | Rhoades et al. . | |
| 5,094,256 | 3/1992 | Barth | 132/322 |
| 5,098,291 | 3/1992 | Curtis et al. | 433/88 |
| 5,127,831 | 7/1992 | Bab | 433/88 |
| 5,261,430 | 11/1993 | Mochel | 132/322 |
| 5,273,428 | 12/1993 | Fischer . | |
| 5,342,195 | 8/1994 | Davis et al. | 433/80 |

*Primary Examiner*—Paul J. Hirsch
*Attorney, Agent, or Firm*—Daniel L. Dawes

[57] ABSTRACT

An apparatus to clean teeth. The apparatus has a reservoir for cleaning liquid and a pump to force cleaning liquid from the reservoir. There is an outlet from the reservoir formed with an attachment. A wand can be attached to the outlet. The wand has an inlet to communicate with the outlet. There is a wand outlet at the distal end of the wand. The wand outlet is dimensioned to ensure that a moderate pressure jet of liquid can be ejected from the outlet. The limb is shaped to allow the jet of liquid to be directed upwardly to the teeth being cleaned and against the gums. In a preferred embodiment, the wand has bifurcated limbs at its distal end and each limb has a wand outlet on an inner surface. The limbs can receive dental floss.

11 Claims, 3 Drawing Sheets

5,570,709

DENTAL DEVICE

FIELD OF THE INVENTION

This invention relates to an apparatus to clean teeth and massage the gums.

DESCRIPTION OF THE PRIOR ART

The traditional way of cleaning teeth has been the use of a brush to which paste is applied. This, in effect, polishes the teeth but its ability to remove food particles from between the teeth is limited.

To cure this deficiency, flossing is now strongly recommended by most dentists. Flossing comprises the drawing of a thread between the teeth to remove particles of food, tartar and the like from between the teeth.

A further approach has been the development of equipment to aim a jet of water at the gaps between the teeth. Such equipment is available under the trademark Waterpik. In this a pump directs a jet of water through a single outlet. The outlet is of small diameter and the jet, usually of water, emerges with considerable pressure.

The use of a water jet and the use of dental floss have undoubtedly been successful. There are, however, disadvantages. In many cases a length of dental floss is gripped between the fingers and forced between the teeth. There is no control of depth and the dental floss can damage the gums between the teeth. Infection can easily develop in that area. Although holders for dental floss, typically of a Y-shaped configuration in which the floss is held between the limbs of the Y, have been used, again there is no attempt to control the depth of insertion of the floss. The same problem of damage to the gums can occur. Typically the limbs of the Y are about a centimetre or more long which means to say there is no control of the depth to which the floss can be inserted.

In the case of a water jet, applicants have noticed that there can be a recession of the gums by people who persistently use water jets for assisting in the cleaning of their teeth. Most people using the jet direct it downwardly against the gum which is, of course, against the natural direction of gum development. Furthermore, as indicated, the jet emerges with considerable pressure that can be strong enough to damage the gum. Gingival pockets and gum recession occur because the jet tends to detach the gum from the tooth.

Combinations of water jets and dental floss are known. Prior art in this field known to applicants includes U.S. Pat. Nos. 5,273,428 to Fischer; 5,094,256 to Barth; 5,033,961 to Kandler; 5,082,444 to Rhoades; 4,031,908 to Ting; 3,472,247 to Borsum and 4,326,549 to Hinding.

Of the above patents, Fischer teaches the arrangement of a cleaning nozzle with a brush. There is no disclosure of dental floss. Barth teaches the use of dental floss with the use of a pressurized fluid supply to produce cleaning by a jet of water and with the floss. Kandler teaches a pump mechanism but there is no disclosure of dental floss. Rhoades teaches a portable mechanism that uses a small supply of compressed air as a means to generate pressure. Ting shows a flossing head and jet of pressurized water. Borsum shows the combination of floss and a water jet and teaches the use of a hand-held valve. Hinding is directed to the mounting of dental floss.

None of the above patents addresses the particular problem of gum damage from the use of floss and, in particular, from the use of a water jet.

SUMMARY OF THE INVENTION

Accordingly applicants wish to provide a simple, portable apparatus, easy to use in a variety of locations, not restricted to use in the home. For example, the apparatus of the present invention can easily be used in the country, after a picnic or the like. Furthermore, and in particular, the apparatus of the present invention has a number of features that prevent damage to the gums either from dental floss or from the use of a water jet.

Accordingly, and in a first aspect, the present invention is an apparatus to clean teeth comprising a reservoir for cleaning liquids;

means to force cleaning liquid from the reservoir;

an outlet from the reservoir formed with attachment means;

a wand to be attached to said outlet;

a wand outlet at the distal end of said wand, said wand outlet being dimensioned to ensure a moderate pressure jet of liquid from said outlet and said limb being shaped to direct a jet of liquid upwardly to the teeth being cleaned and against the gums.

In a further aspect, the present invention is an apparatus to clean teeth comprising:

a reservoir for cleaning liquid;

means to force cleaning liquid from the reservoir;

an outlet from the reservoir formed with attachment means;

a wand to be attached to said outlet and having an inlet to communicate with said outlet and bifurcated limbs at its distal end, each said limb having a wand outlet dimensioned to ensure a moderate pressure jet of liquid from said outlet and being positioned in said limb to direct a jet of liquid upwardly to the teeth being cleaned; and means in said limbs to attach dental floss.

The means to force liquid from the reservoir may be hand-operated pump or an electric pump. In the case of the electric pump the reservoir may include batteries.

DESCRIPTION OF THE PREFERRED EMBODIMENTS

Figure 1:
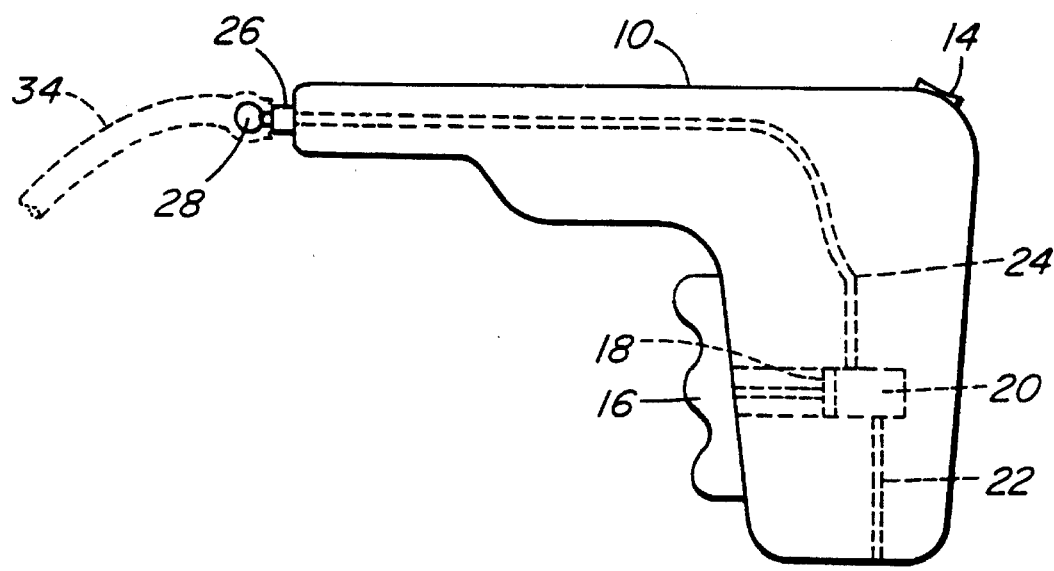
FIG. 1 is a side elevation of one embodiment of the present invention, partially in sections.
Figure 2:
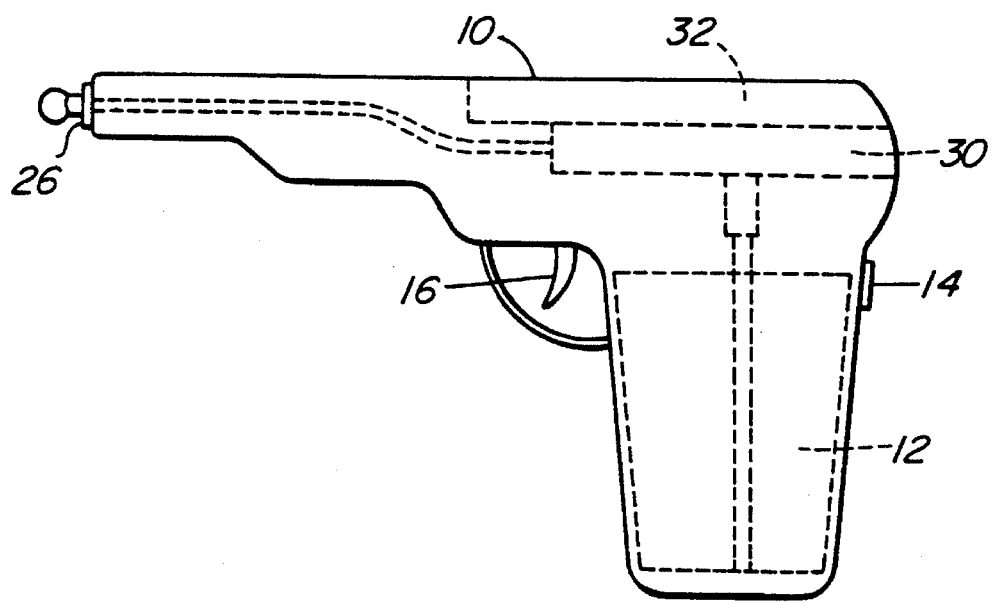
FIG. 2 resembles the embodiment of FIG. 1 but uses a different pump mechanism.

The drawings show an apparatus to clean teeth. In FIGS. 1 and 2, there is a reservoir 10 in the form of a gun, rather like a water pistol, that can hold a cleaning liquid. In many circumstances, it is sufficient that the cleaning liquid be water but, of course, bactericides and the like can also be incorporated into the liquid.

In FIG. 1 the whole interior of the gun contains the liquid. In FIG. 2 there is a tank 12. Inlets 14 are provided in both cases to permit the insertion of the cleaning liquid.

There is means to force the cleaning liquid from the reservoir 10. In FIG. 1 a trigger 16 extends to a piston 18 in a cylinder 20. The cylinder 20 has an inlet tube 22 and an outlet tube 24. Typically check valves, not shown, will be incorporated in these tubes, adjacent the cylinder 20. The piston 18 is moved by a movement of the trigger 16. Movement of the piston 18 to the right of FIG. 1 forces liquid through the outlet tube 24 to an outlet 26 that is formed with an attachment means 28. When the trigger 18 is released, it returns to the position shown in FIG. 1, and in doing so, draws liquid through the inlet tube 22 into the cylinder 20. The apparatus is then ready for re-use either immediately or subsequently. Typically the apparatus will be operated by pumping several volumes of the cylinder against the teeth.

In FIG. 2 the mode of operation is precisely the same except that the trigger 16 operates as a switch to drive an electric pump 30 that pumps liquid from the tank 12 to the outlet 26. A battery compartment 32 is provided to supply power for the electric pump 30. It will be appreciated for use in the home, the battery can be replaced by an adaptor plugged into a conventional electrical socket. Alternatively, a chargeable battery pack can be used.

There is a wand 34 that attaches to the outlet 26. As shown particularly in FIGS. 1, 3 and 4 the wand 34 has an inlet 36 which attaches to the outlet 26 of the reservoir 10 by the attachment means 28.

Figure 4:
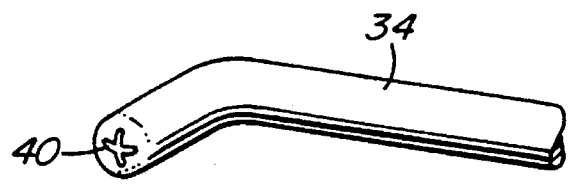
FIGS. 4 and 5 illustrate a wand useful instead of the embodiment of FIG. 3.
Figure 5:
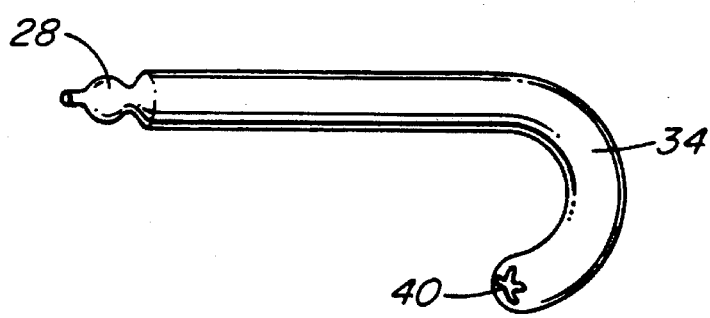

The wand 34 is preferably formed in three parts. A flexible portion is attached to the reservoir 10 which may be attached to a rigid handle (not shown) and then to an outlet or end portion as shown in FIGS. 3 to 6. The flexible portion may, for example, simply be plastic tubing of an appropriate length. The handle will be at least fairly rigid. The outlet of FIGS. 3 and 6 may be rigid but the outlet of FIGS. 4 and 5 is semi-rigid. That is, it can be shaped by hand and will then hold that shape until the user wishes to change it.

Figure 3:
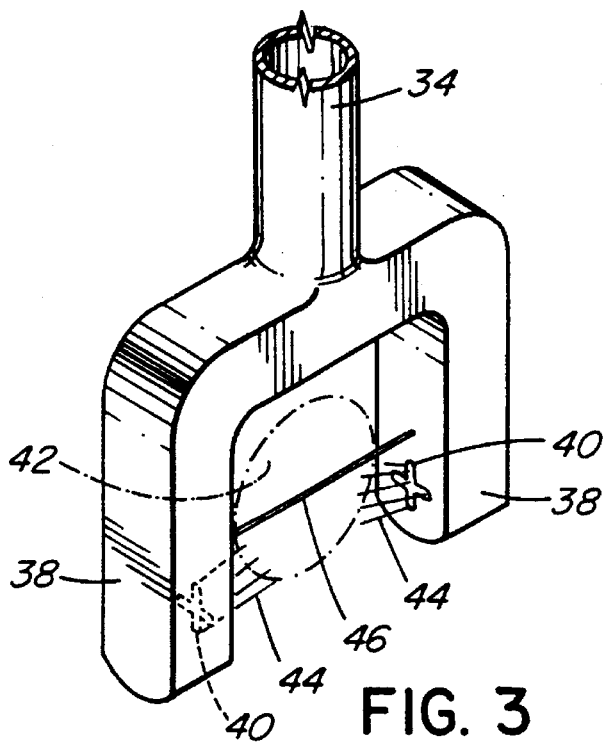
FIG. 3 illustrates a detail of a wand according to a preferred aspect of the present invention.
Figure 6:
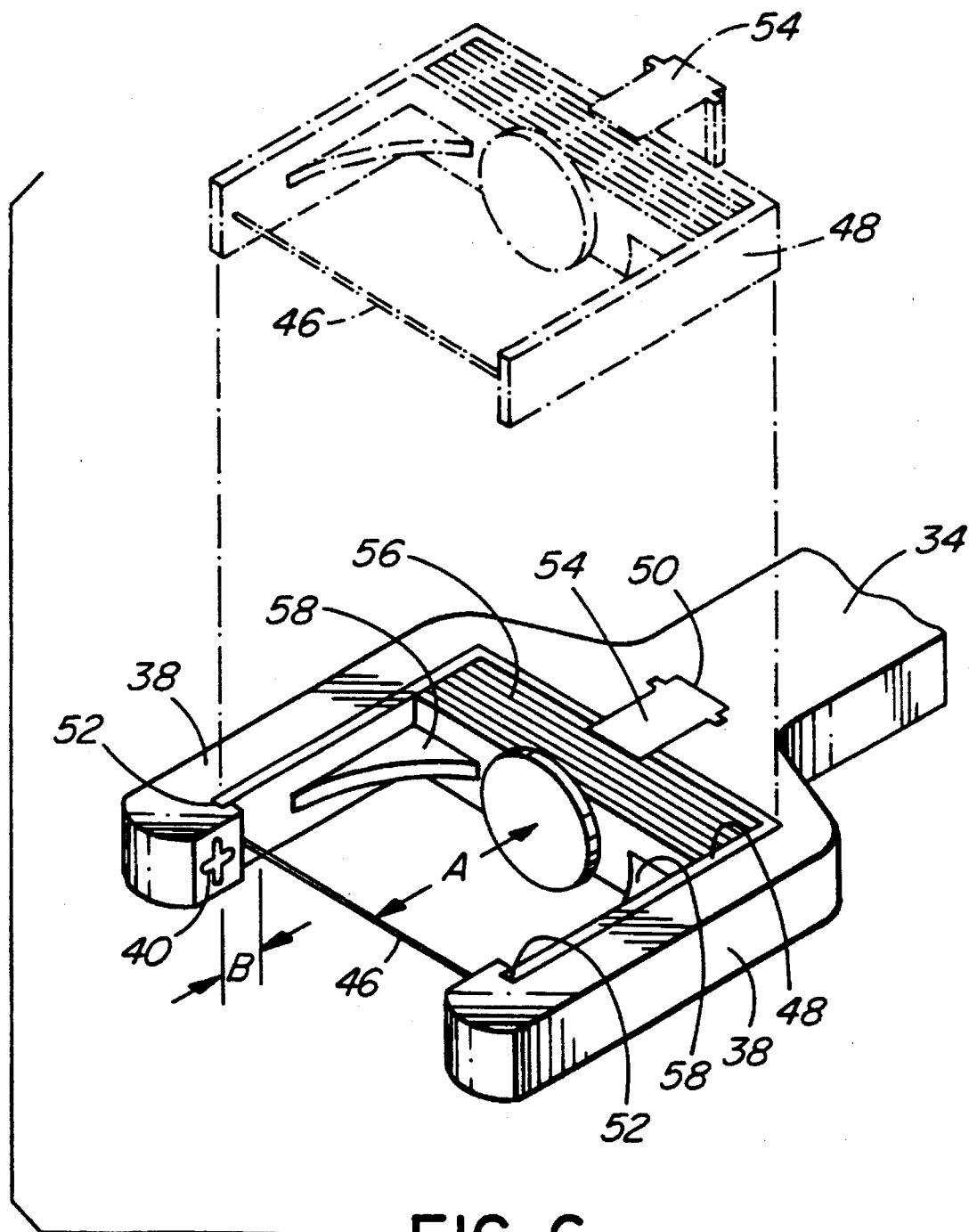
FIG. 6 is a detail of a preferred means of mounting the dental floss.

There are bifurcated limbs 38, as shown particularly in FIGS. 3 and 6 at the distal end of the wand 34. Each limb 38 has a wand outlet 40 as shown particularly in FIGS. 3 and 6. That outlet 40 is deliberately dimensioned to ensure a moderate pressure jet of liquid from the outlet 40. In the preferred embodiment, illustrated in FIGS. 3 and 6, the outlets are cruciform, that is formed of crossed-limbs. It has been found desirable to have the limbs at about 3 to 4 mm in length and with a width of about 0.5 to 0.75 mm. In this manner a satisfactory jet of liquid is provided but not a high pressure jet of liquid.

FIG. 6 shows that the floss 46 is a distance B behind the outlets 40. Distance B is typically such that the floss is about 3 to 4 mm from the ends of the limbs 38, behind the outlets 40 as indicated.

The outlets 40 are positioned in the limbs 38 so that they direct a jet of liquid upwardly to the teeth being cleaned. The arrangement is shown in FIG. 3 where a tooth 42 is shown and liquid 44 is being directed upwardly from the outlets 40 in the direction of growth of the gum. In this way the teeth are cleaned. The space between the teeth are cleared and the gums receive a beneficial massage without the disadvantage of the water jet tending to harm the gums by applying pressure to them in a direction counter to their direction of growth. Preferably the direction is such that the jet of liquid goes at an angle of about 110° to about 120° to a longitudinal or vertical axis of the tooth 42. However, any obtuse angle is appropriate. The important point is to avoid a downward pressure acting to tend to separate the gum from the tooth.

FIG. 6 illustrates a preferred embodiment of the invention in which the means to attach dental floss 46 comprises a frame 48. The frame 48 can be attached and removed from between the bifurcated limbs 38 at the end of the wand 34. In the illustrated embodiment there is a recess 50 in the base of bifurcated limbs 38 and there are recesses 52 adjacent the outer ends of the limbs 38, in the general area of the wand outlets 40. The dental floss 46 is formed on frame 48 which also has a projection 54 that correspond to the recess 50. The ends of the frame 48 are received in the recesses 52 to secure the frame 48 in position. The frame includes a cross piece 56. The distance A from the floss 46 to the cross piece 56 can be controlled. Typically it will be about 6 mm although this can be changed. It should be noted that the frame 48 is cheaply produced in plastic and that the floss 46 will be located on manufacturing. In this way the distance A can easily be controlled. Distance A is a means of controlling the depth of insertion of the floss 46 between the teeth.

Small bracing pieces 58 are also used to stiffen the frame 46.

To operate the apparatus of the present invention, the apparatus is placed in the mouth. The trigger 16 is operated and a jet of water is produced. Simultaneously the floss 46 is moved between the teeth. The depth of insertion is controlled so that the gums are not damaged. Furthermore, the jet of water, issuing from the cruciform outlets 46 is of relatively low pressure, adequate to clean the teeth but not to damage the gums. In this way particles are loosened by the floss and washed away by the jets of water. The gums are massaged by water jet which is known to be beneficial. With the invention, however, the massage is not accompanied by downward pressure on the gum. Furthermore, the force of the water jet when contacting the gum, is distributed on a larger surface and is of lower pressure then prior art jets.

Although the forgoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. Portable, lightweight, apparatus to clean teeth comprising:

An intergral reservoir for cleaning liquid;

means to force cleaning liquid from the reservoir;

an outlet from the reservoir formed with attachment means;

a wand to be attached to said outlet and having an inlet to communicate with said outlet and bifurcated limbs at its distal end, each said limb having a cruciform wand outlet on an inner surface dimensioned to ensure a moderate pressure jet of liquid from said outlet and being positioned in said limb to direct a jet of liquid at an angle of about 110° to 120° to the longitudinal axis of a tooth, away from the gum; and means adjacent to distal end each limb to attach dental floss, said means being positioned further from the distal end of said bifurcated limbs than said outlet.

2. Apparatus as claimed in claim 1 in which the means to force liquid from said reservoir comprises a hand-operated pump.

3. Apparatus as claimed in claim 1 in which the means to force liquid from said reservoir comprises an electric pump.

4. Apparatus as claimed in claim 3 that includes batteries to operate said electric pump.

5. Apparatus as claimed in claim 1 in which the wand includes a flexible portion.

6. Apparatus as claimed in claim 5 in which the wand comprises a separate flexible portion and an end portion, each attachable to each other, the end portion is semi-rigid and thus shapable by the user, the wand including a relatively rigid portion along its length to act as a handle.

7. Apparatus as claimed in claim 5 in which the wand outlets are formed of limbs, each having a length of about 3 to 4 mm and a width of about 0.5 to 0.75 mm.

8. Apparatus as claimed in claim 1 in which the means in said limbs to attach dental flees comprises a frame, that can be attached to and removed from between the bifurcated limbs.

9. Apparatus as claimed in claim 8 in which there is a recess in the base of said bifurcated limbs and recesses adjacent the outer ends of said limbs;

the dental floss being formed on a frame having projections corresponding to said recesses to engage in the recesses in the bifurcated limbs to maintain its position.

10. Apparatus as claimed in claim 9 in which the frame includes a cross piece and in which the distance from the floss to said cross piece is pre-determined to control the depth of insertion of the floss between the teeth.

11. Apparatus as claimed in claim 9 in which there are slots along the interior surface of the limbs to receive the outer surfaces of the frame.

* * * * *